United States Patent
Deitch et al.

(10) Patent No.: US 9,795,483 B2
(45) Date of Patent: Oct. 24, 2017

(54) PEYRONIE'S TREATMENT IMPLANT

(71) Applicant: Coloplast A/S, Humlebaek (DK)

(72) Inventors: Sarah J. Deitch, Minneapolis, MN (US); Julie M. Kerkvliet, Otsego, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 15/201,512

(22) Filed: Jul. 4, 2016

(65) Prior Publication Data

US 2016/0310277 A1    Oct. 27, 2016

Related U.S. Application Data

(63) Continuation of application No. 14/040,696, filed on Sep. 29, 2013, now Pat. No. 9,408,696.

(51) Int. Cl.
*A61F 2/26* (2006.01)
*A61F 2/00* (2006.01)

(52) U.S. Cl.
CPC .............. *A61F 2/26* (2013.01); *A61F 2/0063* (2013.01)

(58) Field of Classification Search
CPC ............... A61B 17/0057; A61F 2/0063; A61F 13/00038; A61F 2013/00829; A61F 2013/00093; A61F 5/41; A61F 2005/411

USPC .............................. 128/897, 898; 600/38–41
See application file for complete search history.

(56) References Cited

U.S. PATENT DOCUMENTS

| | | | | |
|---|---|---|---|---|
| 4,877,030 A | * | 10/1989 | Beck | A61F 2/92 604/913 |
| 5,368,602 A | * | 11/1994 | de la Torre | A61B 17/0057 602/44 |
| 6,042,534 A | * | 3/2000 | Gellman | A61F 2/0045 600/30 |
| 6,176,863 B1 | * | 1/2001 | Kugel | A61F 2/0063 602/44 |
| 2004/0096654 A1 | * | 5/2004 | Morin | C08K 5/0083 428/364 |
| 2009/0228021 A1 | * | 9/2009 | Leung | A61B 17/06166 606/139 |

* cited by examiner

*Primary Examiner* — Samuel Gilbert
(74) *Attorney, Agent, or Firm* — Coloplast Corp. Coloplast A/S; Nick Baumann (57) ABSTRACT

An implant is disclosed. The implant includes a reinforcement component attached to a sheet component. The sheet component is formed as a porous and fibrous material. The implant is adapted to be implanted on an area of a penis having Peyronie's plaques excised. The implant will elongate during erection of the penis and contract when the penis returns to a flaccid state. The reinforcement component includes a longitudinal rod and a transverse connector, with the longitudinal rod providing column strength to the implant and the sheet component providing support for penile tissue.

20 Claims, 11 Drawing Sheets

PEYRONIE'S TREATMENT IMPLANT

BACKGROUND

Peyronie's disease is manifested by an abnormal bend that occurs in the erect penis of the sufferer and can be associated with painful erection and/or painful intercourse.

Peyronie's disease is related to the development of scar tissue, or plaques, that form on tissues (e.g., tunica albuginea) inside the penis. One non-surgical approach for the treatment of Peyronie's disease includes injecting drugs into the plaques that lessen the compression applied by the plaques to the erect penis. The research and efficacy of this approach is limited.

Surgical treatments for Peyronie's disease include excising portions of the tunica albuginea from the penis opposite the plaque and closing the fenestrations with sutures. Access to the tunica albuginea is achieved by first degloving the penile skin away from the penis to expose the Buck's fascia and tunica albuginea along the length of the penis. Degloving the penile skin is painful and the recovery time for the patient can be several weeks. Although the long term results of this surgical approach are good, both short term (within 8 weeks) and long term failures can present with residual penile deformity.

Another surgical treatment includes corporal plication in which plication sutures are placed on the contralateral side of the plaque without excising the tunica albuginea or removing the plaque. Corporal plication is most commonly employed subsequent to a previous Peyronie's treatment surgery to correct small angles of residual penile deformity.

Patients and clinicians desire more effective treatments for Peyronie's disease.

SUMMARY

One aspect provides an implant that includes one or more sheet components attached to at least one reinforcing component. The at least one reinforcing component provides column strength to the implant and the one or more sheet components provides support for penile tissue. The implant is adapted to be positioned on a Peyronie's plaques affected area of a penis. The implant is configured to elongate during an erection of the penis and to contract when the penis returns to its flaccid state.

One aspect provides an implant for treatment of Peyronie's disease. The implant includes a skeletal framework having one or more sheet components attached to at least one reinforcing component to support penile tissue and to provide a flexible, yet strong and durable implant. The sheet components are at least partly made from a biocompatible material. The implant is placed subcutaneously on an affected area of the penis. The skeletal framework of the implant allows for elongation of the implant during erection of the penis and for contraction of the implant when the penis is returning to its flaccid state. To secure the implant to the penis, the skeletal framework includes at least one attachment mechanism.

One aspect provides an implant that includes a skeletal framework having one or more sheet components attached to a plurality of reinforcing components that provide column strength along a longitudinal direction of the implant and the sheet components provide support for penile tissue. The skeletal framework of the implant allows for elongation of the implant during erection of the penis and for contraction of the implant when the penis is returning to its flaccid state.

One aspect provides an implant that includes a skeletal framework having one or more sheet components attached to at least one reinforcing component that provide support for penile tissue and column strength to the implant, respectively. The implant is configured to be placed underneath the upper skin layer of the penis (e.g. on the tunica albuginea, T.A.) on an affected area of the penis and forms an arch describing 180 degrees or less.

One aspect provides an implant that includes a skeletal framework having one or more sheet components attached to a plurality of reinforcing components and at least one attachment mechanism including a suture line attached to the skeletal framework at one end and a hook-shaped needle for tissue penetration attached at a second end of the suture line and at least one anchor provided on the suture line for securing the implant to the penis.

One aspect provides a method of treating Peyronie's disease. The method includes implanting an implant including one or more sheet components attached to a reinforcing component. The method includes performing an incision to gain access to the penile tissue affected by the Peyronie's plaques and excising the scar tissue. The method includes providing the implant on the affected area. The method includes positioning the implant so as to provide for optimal tissue ingrowth and for optimizing column strength in the implant. The method includes securing the implant to the penis. The method includes closing the incision.

Embodiments provide an implant that eliminates or reduces the physical effects of the Peyronie's disease. Embodiments of the implant described in this application have improved sustainability and durability and thus reduces or eliminates the potential for surgical revision and/or substitution of the implant. A further object is to provide a Peyronie's treatment implant that is easily manageable and has improved flexibility in order to improve patient perception and comfort. A further object is to provide an implant that supports and reinforces the affected penile tissue area where the plaques have been removed. A still further object is to provide an implant that is easily implantable and obviates the use of other tools to attach the implant to the penile tissue. A further objective is to provide another alternative to a medicament based treatment option for Peyronie's disease.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes.

Anterior means "forward" or "front," and posterior means "rearward" or "back." Relative to surfaces of an organ in the human body, an anterior surface is oriented forward toward the belly and a posterior surface is oriented rearward toward the spine.

The term "proximal" as employed in this application means that part that is situated next to or near the point of attachment or origin or a central point: as located toward a center of the human body. The term "distal" as employed in this application means that part that is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal and of the crus of the penis is located proximal relative to the male body such that a distal end of a corpora cavernosum of the patient extends about midway into the glans penis.

Figure 1A:
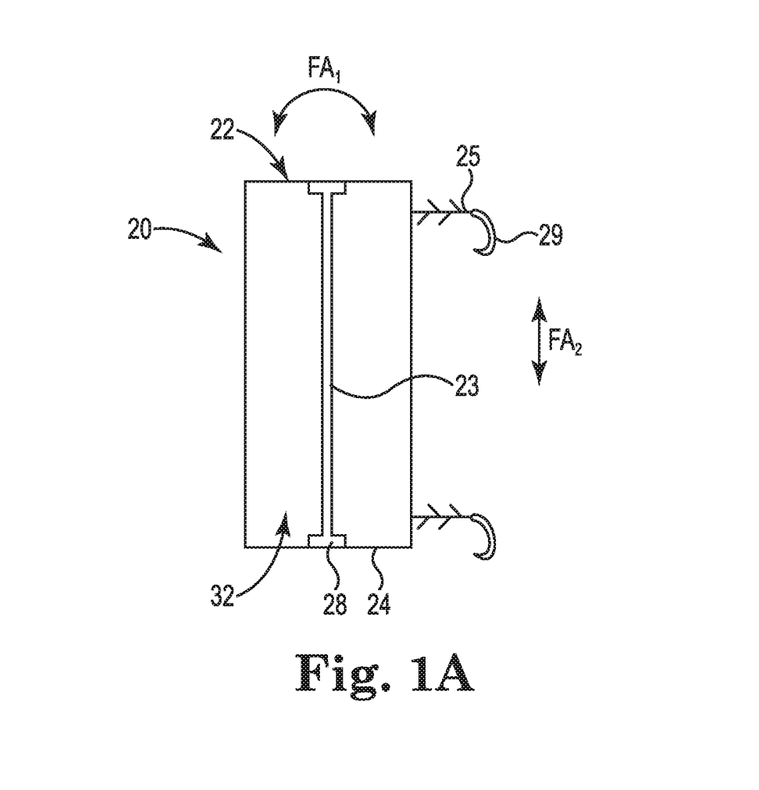
FIG. 1A is a top view of one embodiment of an implant.

FIG. 1A is a top view of one embodiment of an implant 20 for treating Peyronie's disease. The implant 20 includes at least one reinforcing component 22 attached to a sheet component 32. In one embodiment, the implant 20 includes two or more sheet components 32. The sheet component(s) 32 are fabricated to reduce the build-up of new scar tissue around the implant 20, which promotes new tissue generation surrounding the implant 20 resulting in stronger and more durable regenerated tissue. The sheet component 32 is selected to be bio-compatible with implantation into a human body and is configured to be porous to allow tissue ingrowth throughout its structure and thus anchor the sheet component 32 in the body after implantation and healing. Suitable sheet component 32 include autograft material (the patient's own tissue), allograft material (tissue from a cadaver), xenograft material (tissue from another species), or synthetic materials such as woven fabrics, meshes, non-woven fabrics, meshes, fibrillated fibers, or spun and fibrillated fibers that are provided with voids (pores) configured to allow tissue ingrowth into the sheet component 32. The pores are generally larger, on average, than 75 µm.

The implant 20 is flexible laterally and longitudinally, e.g., in directions indicated by arrows $FA_1$ and $FA_2$ and thus configures to elongate during an erection of the penis and contract when the penis returns to its flaccid state. The implant 20 is adapted to be positioned on an area of a penis from where the Peyronie's plaques or scar tissue has been excised (see also FIGS. 1C-1E). The reinforcing component 22 provides column strength to the implant 20 and the sheet components 32 provides support for penile tissue.

The illustrated skeletal framework 21 includes an attachment mechanism 25 for securing the implant 20 to the penis. The attachment mechanism 25 includes a barbed line 25 and a needle 29. The barbed line 25 is configured to glide smoothly and easily in an insertion direction into tissue (i.e., the barbed line 25 has low resistance going into the tissue). Conversely, the barbed line 25 is configured to resist movement of the attachment mechanism 25 in an extraction direction from this tissue. The needle 29 is provided to guide the barbed line 25 into the tissue, after which the needle 29 is removed, leaving the barbed line 25 secured within the tissue. The illustrated embodiment includes a skeletal framework 21 wherein the distal and/or the proximal ends of at least some of the reinforcing components 22 are defined by a radially extending flange 28. This will be explained in more detail below.

Figure 1B:
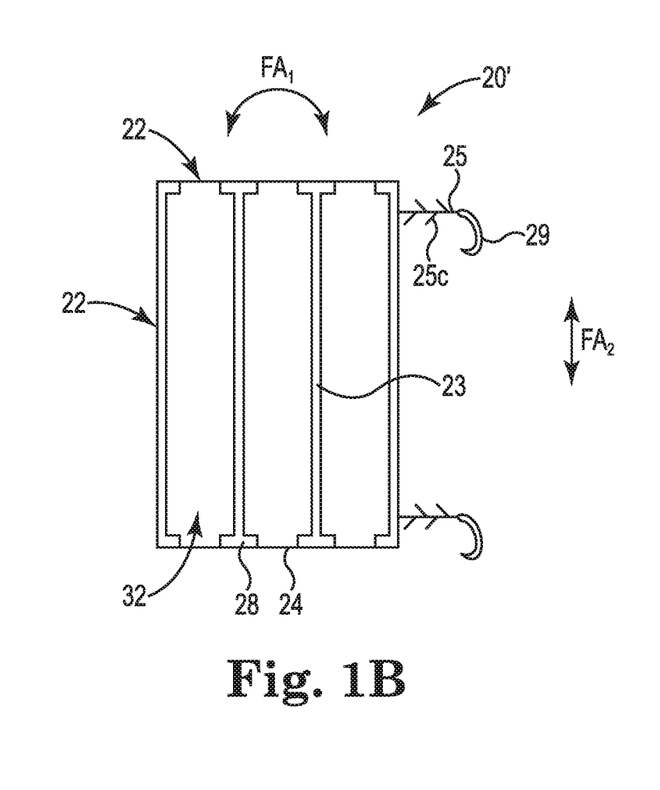
FIG. 1B is a top view of one embodiment of an implant.

FIG. 1B is a top view of one embodiment of an implant 20'. The implant 20' includes a skeletal framework 21 including one or more of the sheet components 32 described above attached to at least one reinforcing component 22. The implant 20' is flexible laterally and longitudinally, e.g., in directions indicated by arrows $FA_1$ and $FA_2$. The sheet components 32 of the implant 20 include a biocompatible material which reduces the build-up of scar tissue around the implant 20 and promotes new tissue generation surrounding the implant 20 resulting in stronger and more durable regenerated tissue. The components 22 and 32 provide a biocompatible and flexible, but relatively strong and durable implant 20 that is implanted in the penis P after the excision of the Peyronie's plaques. The illustrated skeletal framework 21 includes an attachment mechanism 25 for securing the implant 20 to the penis. In FIG. 1B, the distal and/or the proximal ends of at least some of the reinforcing components 22 are defined by a radially extending flange 28.

Embodiments include reinforcing components 22 configured to include longitudinal rods 23 and transverse connectors 24.

Figure 1C:
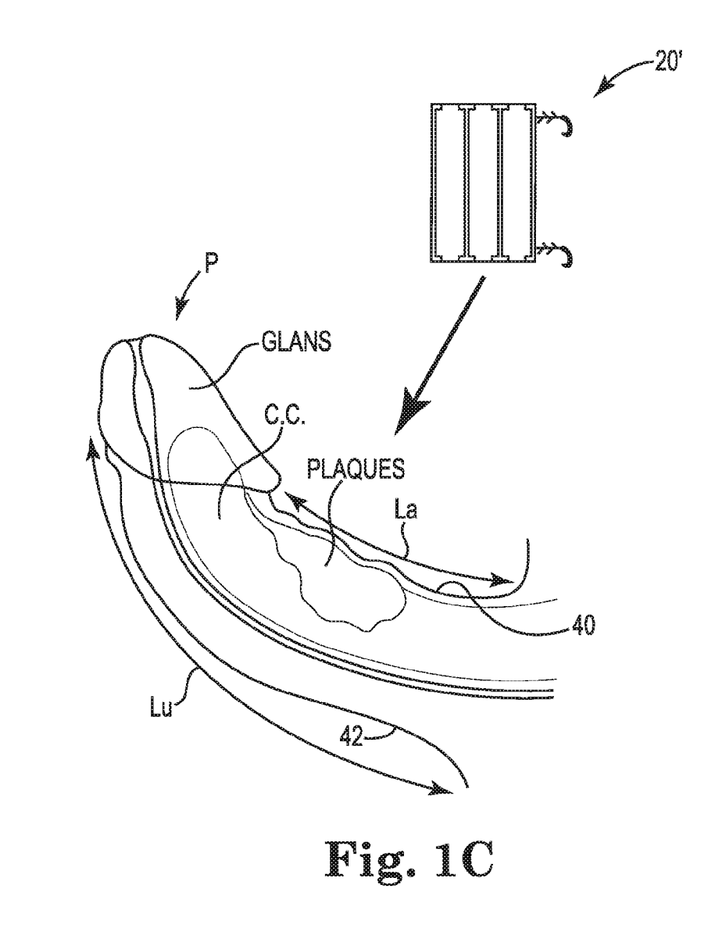
FIG. 1C is a perspective view of an erect penis afflicted by Peyronie's disease indicating where the implant of FIG. 1B is to be applied on the penis.
Figure 1D:
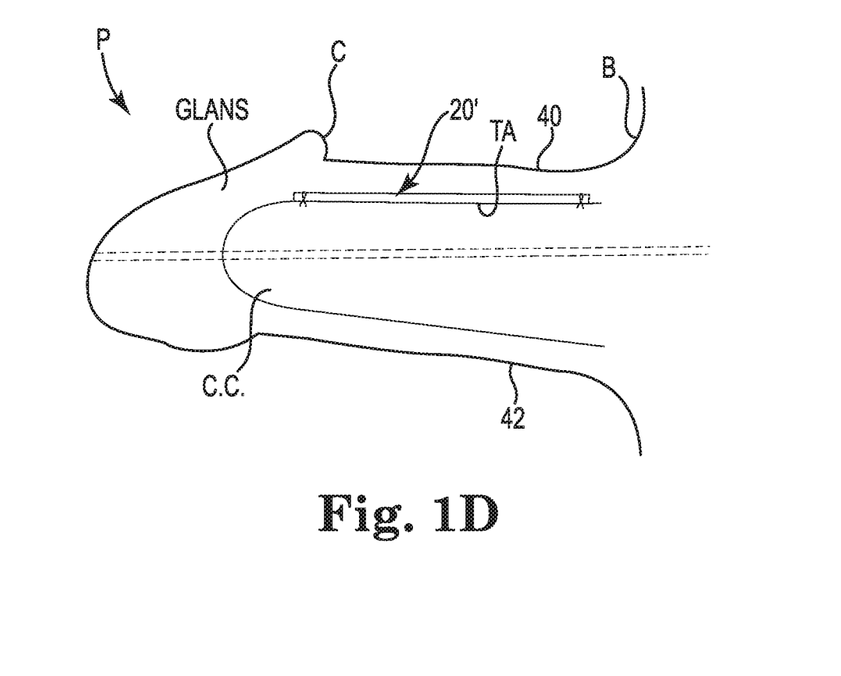
FIG. 1D is a side schematic view of the penis illustrated in FIG. 1C in a flaccid state and including an implant attached to the tunica albuginea of the penis.
Figure 1E:
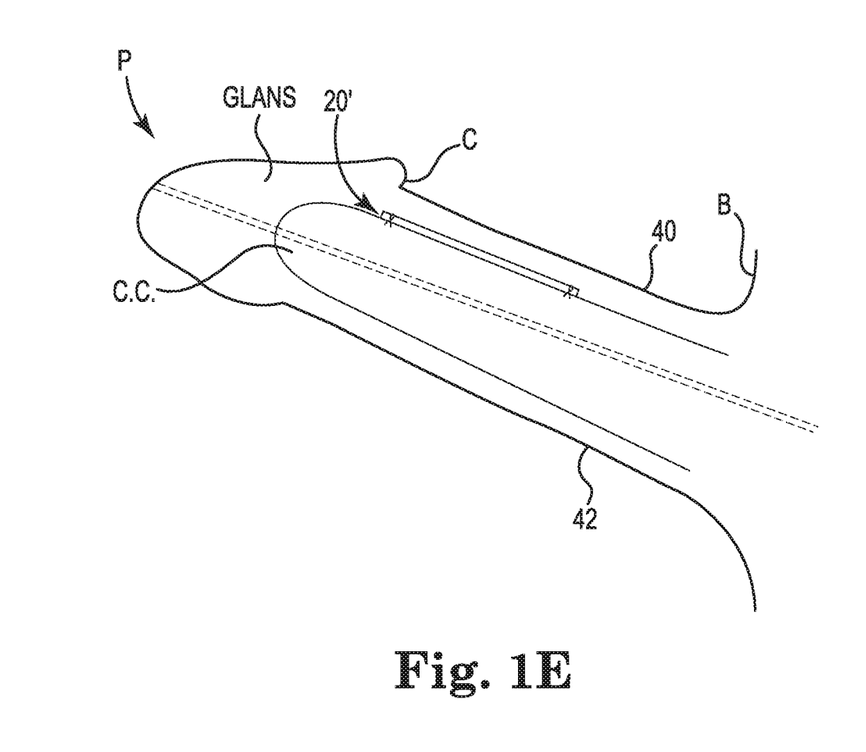
FIG. 1E is a side schematic view of the penis illustrated in FIG. 1D in an erect state having reduced curvature as compared to the untreated penis illustrated in FIG. 1C.

FIG. 1C is a perspective view of an erect penis afflicted by Peyronie's disease, FIG. 1D is a side view of the flaccid penis treated with the implant 20', and FIG. 1E is a side view of the erect penis supported by the implant 20'. Patients who suffer from Peyronie's disease develop a curvature in the erect penis often manifested in one side of the penis having an unaffected length and, generally, an opposite side of the penis having an affected length that is shorter than the unaffected length of the penis. The implant 20' is configured to be implanted in the penis P to alleviate this condition. In embodiments, the skeletal framework 21 has a length that is selected to stretch between a first initial length in its position covering at least a portion of the excised plaques area between a base B of the penis P and a corona C of the penis when the penis is flaccid to a final length that is approximately equal to the plaque affected length of the penis. The skeletal framework 21 is thus configured to move with the penis P between its flaccid state and its erect state, and when the penis is erect, the implant 20' is configured not only to support the penile tissue but also to straighten the penis P to an approximately symmetric shape/length (FIG. 1E).

The implant 20' is attached subcutaneously to an exterior surface of the tunica albuginea TA at least on an affected area 40 of the penis P from which the Peyronie's plaque has been excised, and functions to support the exposed penile tissue and to keep the penis straight during an erection. The skeletal framework 21 is fabricated from materials that provide for the implant to be elongatable during an erection of the penis and correspondingly contractible when the penis returns to its flaccid state and are biocompatible.

Embodiments include materials having shape memory. The shape memory material has at least two stable states. This includes a first state corresponding to a flaccid state of the penis and another state when the penis is erect. When exposed to an external force such as heat or electricity, the material changes between its stable states. In other words, shape memory materials have the ability to return or recover to their original shape at the presence of the right stimulus, such as a heat or strain influence. One example of such a force in terms of heat could be when blood flows into the corpora cavernosum to create an erection of the penis. This blood flow causes the surrounding tissue of the penis to increase in temperature, which in turn changes the state of the shape memory material. This provides an implant that suitably configures to further support or sustain a straight erection of a penis. Configuring the shape memory material such that it changes state to a straight or stretched configuration when influenced by the warm blood flow of the erection provides an implant that supports a straight erection of the penis.

Suitable materials for fabricating the reinforcing components 22 of the implant 20 configured by the longitudinal rods 23 and the transverse connectors 24 include biocompatible materials such as Nitinol, a metal alloy of nickel and titanium also having shape memory and superelasticity characteristics, or a shape memory polymer, e.g. based on polyurethane.

Figure 2A:
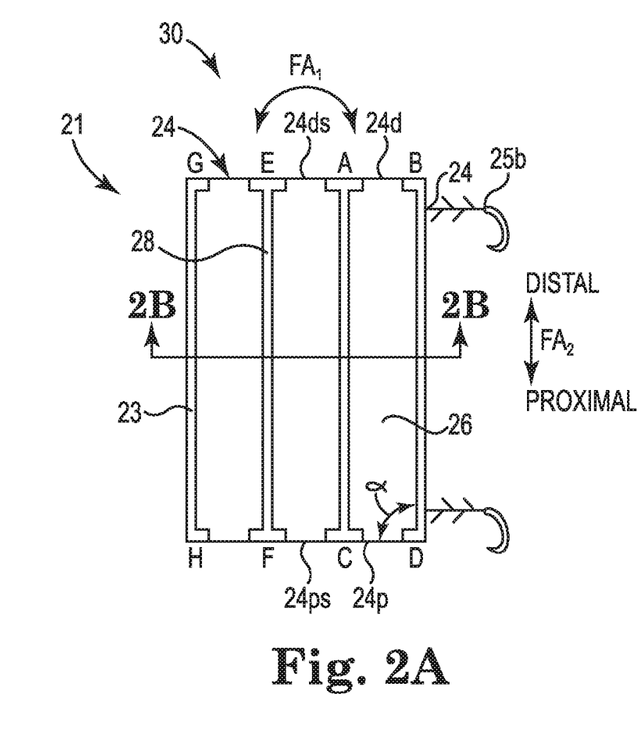
FIG. 2A is a schematic top view of one embodiment of reinforcing components of a skeletal framework and an attachment mechanism of an implant.

FIG. 2A is a top view of one embodiment of an implant 30. The implant 30 includes reinforcing components 22 of a skeletal framework 21 and an attachment mechanism 25.

The components 22 of the skeletal framework 21 are assembled to provide at least one substantially rectangular framework ABCD. "Substantially rectangular" means that the reinforcing components 22 of the implant 30, including the longitudinal rods 23 and the transverse connectors 24, are arranged at an angle α in a range of approximately 85-95 degrees in relation to each other. A first transverse connector 24d is attached to the distal ends of two neighboring longitudinal rods 23 and a second transverse connector 24p is attached at the proximal, or opposite, ends of the neighboring longitudinal rods 23.

Embodiments include a skeletal framework 21 having further longitudinal rods 23 and transverse connectors 24 configuring, more than one rectangular framework. To accommodate differences in size of Peyronie's plaque affected areas of penile tissue on individual patients, the number of reinforcing components 22 suitably includes more than two longitudinal rods 23 and two transverse connectors 24. FIG. 2A illustrates, as an example, three rectangular frameworks ABCD, EAFC and GEHF arranged in a side-by-side configuration. In FIG. 2A, longitudinal rod 23 extending between positions A and C configures to be part of both rectangular framework ABCD and EAFC, or can be said to be shared between those rectangular frameworks. Similarly, longitudinal rod 23 extending between positions E and F is part of both rectangular frameworks EAFC and GEHF. Embodiments include a skeletal framework 21 wherein more than one, or all longitudinal rods 23 are attached to a single transverse connector 24ds at their distal ends and correspondingly to another single transverse connector 24ps at their proximal ends.

Figure 2B:
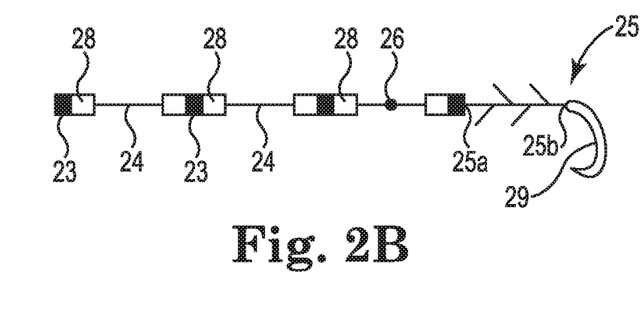
FIG. 2B is a schematic side view of the embodiment illustrated in FIG. 2A.

FIG. 2B is a cross-sectional view of the implant 30 illustrating an embodiment in which the transverse connectors 24 include a link 26 that pivots to provide additional flexibility to the implant 30. FIG. 2B also illustrates the attachment mechanism 25 attached to a longitudinal rod 23.

Figure 2C:
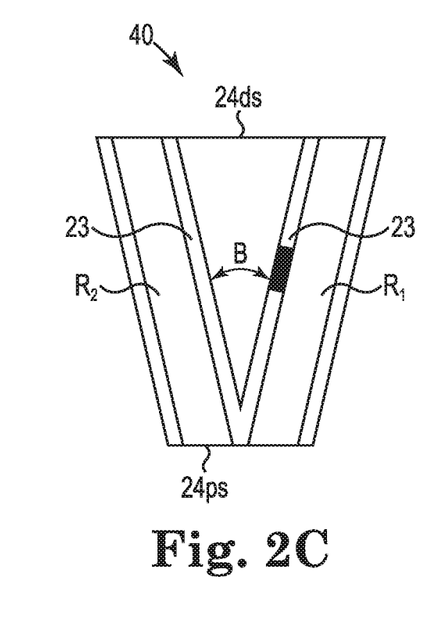
FIG. 2C is a schematic view of one embodiment of an implant.

FIG. 2C is a top view of an embodiment of an implant 40 with the skeletal framework 21 assembled in two rhomboids R1,R2. The rhomboids R1,R2 are arranged with an angle β between rhomboid R1 and rhomboid R2. For example, the longitudinal rod 23 of one rhomboid R1 is at an angle β with a longitudinal rod 23 of a second rhomboid R2. This provides a flexible implant 40 having a larger width $L_2$ at one (e.g. proximal) end of the longitudinal rods 23 of the skeletal framework 21 and a shorter length $L_1$ at the opposing (e.g. distal) end. In embodiments, the rhomboids R1,R2 share the same single transverse connectors 24ds, 24ps at their distal and proximal ends, respectively. However, the rhomboids R1,R2 suitably each include individual transverse connectors 24 at their distal and proximal ends.

In embodiments, the skeletal framework 21 configures as at least one rhomboid in which the longitudinal rods 23 and transverse connectors 24 are arranged at angles being less than 85 and more than 95 degrees.

Figure 2D:
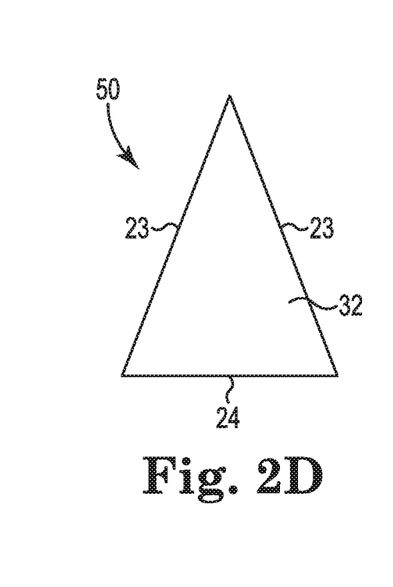
FIG. 2D is a schematic view of one embodiment of an implant.
Figure 2E:
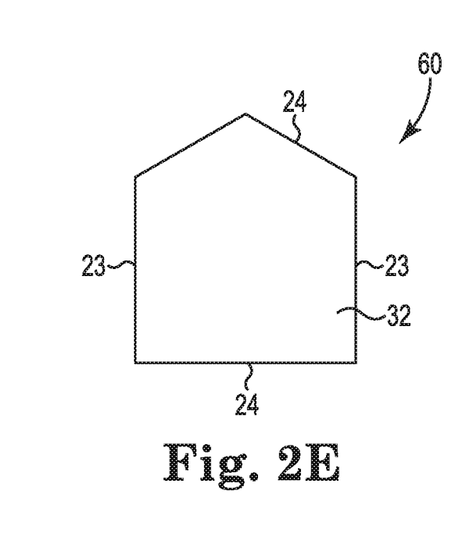
FIG. 2E is a schematic view of one embodiment of an implant.

FIG. 2D is a top view of one embodiment of an implant 50 and FIG. 2E 2D is a top view of one embodiment of an implant 60. These implants 50, 60 likewise include a skeletal framework including an uneven number of longitudinal rods 23 and transverse connectors 24. This includes configuring different polygon shapes of the implants 50, 60 such as, but not limited to, triangles and pentagons. In FIG. 2D, the plurality of reinforcing components 22 of the skeletal framework of the implant 50 has at least three reinforcing components including two longitudinal rods 23 and one transverse connector 24 so as to provide a triangular configuration of the implant 50. Embodiments include one or more longitudinal rods coupled with one or more transverse connectors. In some embodiments, the transverse connectors 24 include one or more pivotable links 26 (FIG. 2B) between and/or at their opposing ends, thereby providing additional flexibility to the implant 20.

Figure 3A:
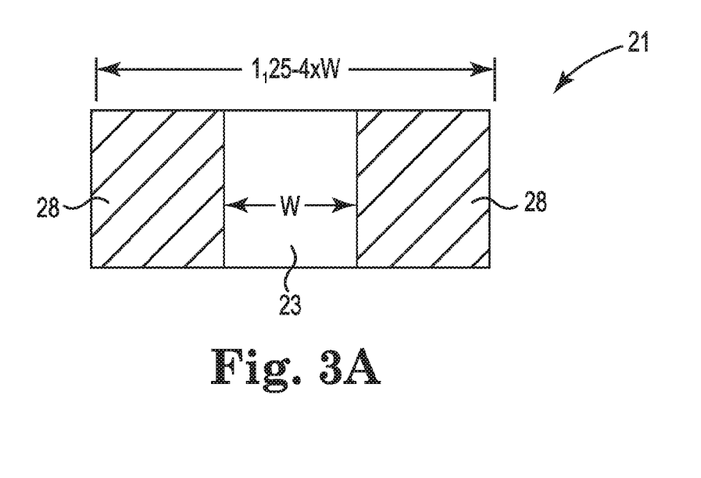
FIG. 3A is an enlarged, schematic cross-sectional view of one embodiment of a reinforcing component configured as a rectangular rod including a radially extending flange at an end.
Figure 3B:
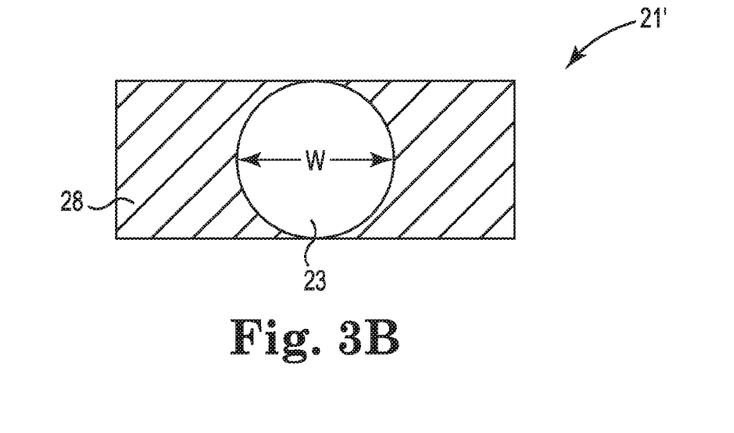
FIG. 3B is an enlarged, schematic cross-sectional view of one embodiment of a reinforcing component configured as a circular column including a radially extending flange at an end.

As further illustrated in FIGS. 1A, 1B, 2A and 2B, embodiments include a skeletal framework 21 wherein the distal and/or the proximal ends of the longitudinal rods 23 are defined by a radially extending flange 28. This is further illustrated in the schematic cross-sectional view of FIG. 3A. The flange 28, or flanges, if both the distal and the proximal ends of the longitudinal rods 23 are configured to include a flange, has a total extent in a crosswise direction of the longitudinal rod 23 of 1.25-4 times the width w of the longitudinal rod 23. Embodiments also include a skeletal framework 21' having longitudinal rods 23 configured as circular columns 27 as indicated in FIG. 3B. The columns 27 include diameters in the range of 0.01-1.0 mm.

In the case of longitudinal rods 23 configured as circular columns 27 the width w corresponds to the diameter of the column 27.

Embodiments also include a skeletal framework 21 wherein the reinforcing components 22 are injection molded. Configurations wherein some of the reinforcing components 22 are injection molded and some are fabricated otherwise, such as by casting or extrusion, are also included. Embodiments include a skeletal framework 21 wherein the reinforcing components 22 are injection molded as an integrated frame ABCDEFGH (FIG. 2A). Material examples for injection molded reinforcing components 22 include thermoplastics such as polyethylenes or polypropylenes.

Embodiments include a skeletal framework 21 wherein the transverse connectors 24 are attachable to the radially extending flange 28, or flanges, of the longitudinal rods 23 and/or vice versa. Attaching the transverse connectors 24 and the longitudinal rods 23 at the radially extending flanges 28 provides a flexible, yet stable and strong skeletal framework 21 for reinforcement of the implant 20. In embodiments, the reinforcing components 22 of the skeletal framework 21 are attached to each other by a suitable type of welding, gluing or other type of mechanical connection. As illustrated in several figures, embodiments include an implant 20 wherein an attachment mechanism 25 is provided on the skeletal framework 21 to attach the implant 20 to the penis P. In contrast to providing a separate needle and suture for attachment of the implant to the tissue, embodiments provide an implant 20 including such attachment means that provides the surgeon with a more flexible choice in regard to positioning the implant 20 on the penile tissue. Embodiments provide an implant 20 that can be attached to whatever portion of the penile tissue that is desired. Furthermore, this reduces the need for additional surgical equipment and also reduces the need for assistance for the surgeon. Embodiments include an attachment mechanism 25 having a first end 25a being fixedly connected to a first longitudinal rod 23 and a second end 25b. This includes embodiments wherein the implant 20 is attached to the penis P without penetrating tissue instead the attachment mechanism 25 attaches onto the implant 20 itself such as, but not exclusively, in a cylindrical configuration of the implant 20 as illustrated in FIG. 5B.

With reference to FIGS. 2A and 2B, the attachment mechanism 25 is configured by a suture line 25c having a detachable needle 29 at a second end 25b so as to attach the implant 20 to the penis P by suturing it on to the penile tissue. In embodiments, the detachable needle 29 includes a hook-shaped surgical needle. The needle 29 is configured to penetrate a targeted tissue to be able to pull the suture line 25c through penetrated tissue. The needle 29 is suitably attached to the suture line 25c at the first end 25a by tying a knot or in other suitable ways. In embodiments, the needle 29 is detached by cutting the suture line 25c or untying the knot at the first end 25a. In embodiments, one or more anchoring barbs 31 are configured along the suture line 25c between the first and second ends 25a, 25b. The anchoring barbs 31 include several single-side tapered protrusions extending radially from the suture line 25c to provide stopping surfaces to prevent the anchoring barbs 31 (and thus the suture line 25c) from slipping backwards once having been pulled through the penetrated tissue. In embodiments, the anchoring barbs 31 are provided as one or more separate elements attachable to the suture line 25c. In embodiments, the anchoring barbs 31 are made integral with the suture line 25c. In embodiments, the second end 25b of the attachment mechanism is configured by a second end of the suture line 25c that is attachable to another, or different, component of the implant. Embodiments include an attachment mechanism at least partly made from one or more biocompatible material which may also be absorbable in the body.

Figures 4A, 4B, 4C, 4D:
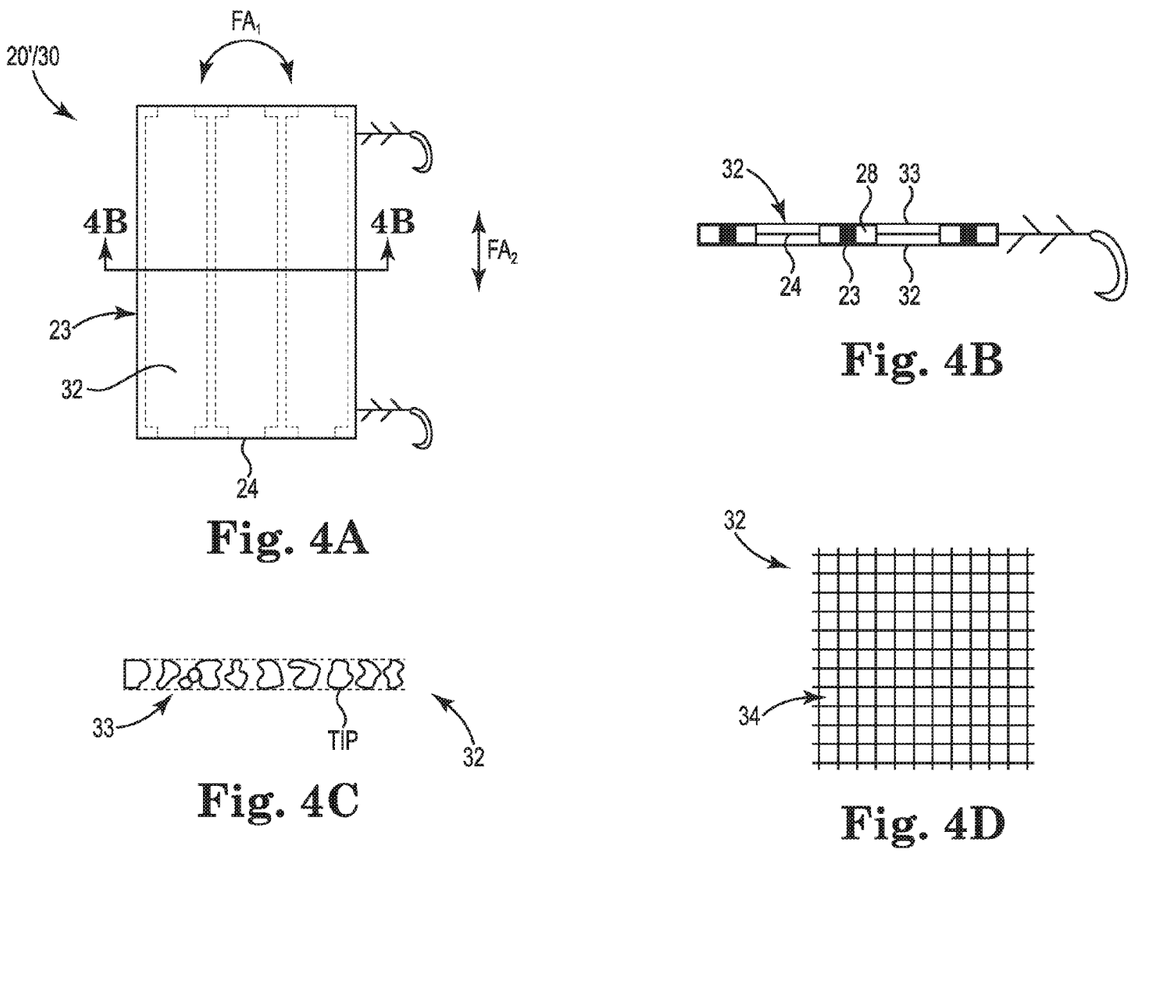
FIG. 4A is a schematic top view of one embodiment of an implant including a skeletal framework having sheet components attached to reinforcing components.
FIG. 4B is a schematic side view of the implant as illustrated in FIG. 4A including longitudinal rods of the reinforcing components configured as circular columns and sheet components enclosing the reinforcing components.
FIG. 4C is a schematic side view of one embodiment of a sheet component configured as a porous support.
FIG. 4D is a schematic top view of one embodiment of a sheet component configured as a mesh or mesh-like structure.

FIG. 4A is a schematic top view of an embodiment of the implants 20'/30. FIG. 4B is a schematic cross-sectional view of the implants 20'/30. The figures include an illustration of the sheet components 32 of the implant 20 that are at least partly made from a fibrous and porous biocompatible material which reduces the build-up of fibrosis tissue around the implant 20 and promotes new tissue generation by improved re-epithalization of cells surrounding the implant 20 resulting in stronger and more durable regenerated tissue. FIG. 4B illustrates sheet components 32 surrounding or enclosing the reinforcing components configured by longitudinal rods 23 and transverse connectors 24. In embodiments, the sheet components 32 are configured as a single individual sheet. In other embodiments, the one or more sheet components is/are configured as at least one sheath. This sheath configures an envelope for at least partly enclosing the reinforcing components 22.

In embodiments, the sheath components 32 of the implant 20 include porous supports 33. Porous supports 33 include sheet components 32 including a material that is capable of supporting penile tissue while still being at least partly open pored or having wholly or partly through-going pores to provide for ingrowth of penile tissue into and/or through the sheet components 32 as shown in FIG. 4C. Spanning the implant 20 by means of the skeletal framework 21 having the sheet components 32 configured between the reinforcing components 22 to support the penile tissue provides for a very flexible, yet durable and strong implant 20 that facilitates and/or improves potential ingrowth of regenerated tissue and reduces bulkiness of the implant and improves patient comfort. In embodiments, the reinforcing components 22 of the skeletal framework 21 are covered by the porous supports 33, either partly or wholly such as by enclosing the reinforcing components 22 between two layers of porous support 33 or by enveloping the reinforcing components 22 in the porous supports 33. In embodiments, the porous supports 33 include pericardium tissue. The pericardium tissue may be chosen from a variety of sources including human or bovine pericardium tissues. Alternatively, the porous supports 33 include artificially grown tissues and/or fabricated mesh-like structures 34 (FIG. 4D). Fabricated mesh-like structures 34 include materials such as polyethylenes or other biocompatible material components. Suitable materials for the mesh-like structures include high-density polyethylene fiber substrates such as TYVEK® available from DuPont™ or TUTOPLAST® processed pericardium available from Coloplast Corp., Minneapolis. In embodiments including a rhomboid configuration of the skeletal framework 21 of the implant 20, the angular space spanned by the angle β between neighboring longitudinal rods 23 of the rhomboids R1,R2 (FIG. 2C) suitably additionally include one or more sheet components 32, such as a porous support 33.

In embodiments, the sheet components 32 and/or the reinforcing components 22 of the implant include materials that are absorbable in the human body over an approximate pre-determined time. One suitable implant 20 is fabricated wholly or in part from absorbable components. Suitable materials for the sheet components 32 and/or for the reinforcing components 22 of the implant 20 include materials that provide for a permanent and stable implant in order to sustain the effect of the implant 20 for as long as desired. In some embodiments, the sheet components 32 of the implant 20 suitably are configured to be exchangeable while the reinforcing components 22 are configured to be maintained or re-used with the exchanged sheet components 32.

In embodiments, the sheet components 32 include one or more tissue-ingrowth promoters TIP. In embodiments, the tissue-ingrowth promoters TIP are coated onto the sheet components 32. The tissue-ingrowth promoters TIP are included to support or enhance the re-epithalization of cells to help regenerate and reinforce penile tissue and/or reduce the length of the rehabilitation period after surgery. One example of a tissue-ingrowth promoter TIP includes platelet-rich plasma.

Figure 5A:
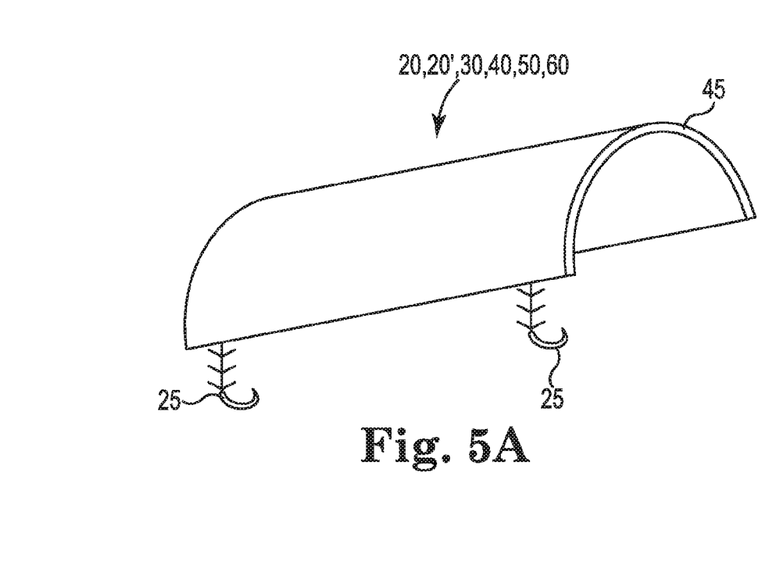
FIG. 5A is a perspective view of one embodiment of an implant.
Figure 5B:
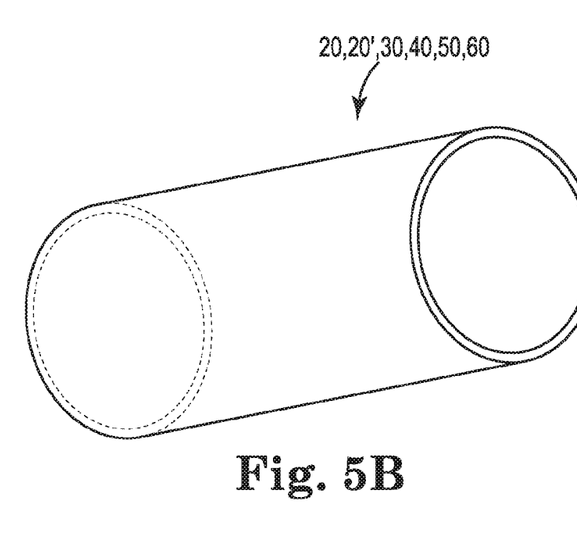
FIG. 5B is a perspective view of one embodiment of an implant.

FIG. 5A illustrates one embodiment where an individual one of the implants 20, 20', 30, 40, 50, 60 described above form an arch 45 describing 180 degrees or less. The implants 20, 20', 30, 40, 50, or 60 includes the attachment mechanism 25. The implant 20 is suitably partly or wholly configured to follow at least a part of a circumferential curvature of the exposed penile tissue.

FIG. 5B is a schematic illustration of an embodiment where an individual one of the implants 20, 20', 30, 40, 50, or 60 described above is provided in a cylindrical configuration. Some patients may require substantial removal of Peyronie's plaques over a tissue area of more than half the circumference of the penis for which a cylindrical implant of the embodiment of FIG. 5B is appropriate.

Figure 5C:
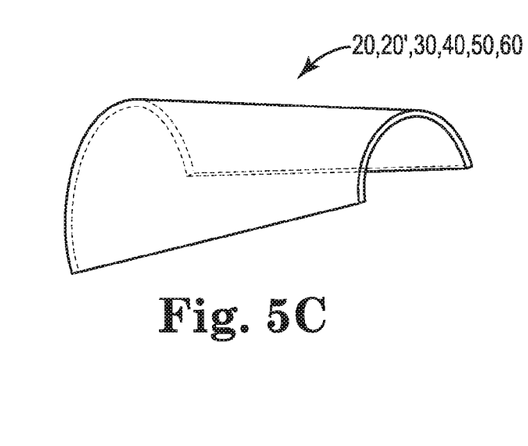
FIG. 5C is a perspective view of one embodiment of an implant.

FIG. 5C illustrates a perspective view of an embodiment where an individual one of the implants 20, 20', 30, 40, 50, or 60 described above are formed to provide a semi-circular or arch configuration 45 of the implant 20 of FIG. 5A combined with the disclosed rhomboid configuration of the skeletal framework 21 (FIG. 2C) providing a flexible implant 20 having a larger width at one (e.g. proximal) end of the longitudinal rods 23 of the skeletal framework 21 and a shorter length at the opposing (e.g. distal) end thereof. This provides an additional flexibility in regard to choice of size and positioning of the implant 20, particularly if the plaques affected area of the penile tissue is irregularly shaped or has been irregularly excised and is following at least some circumferential curvature of the penile tissue.

Figure 6:
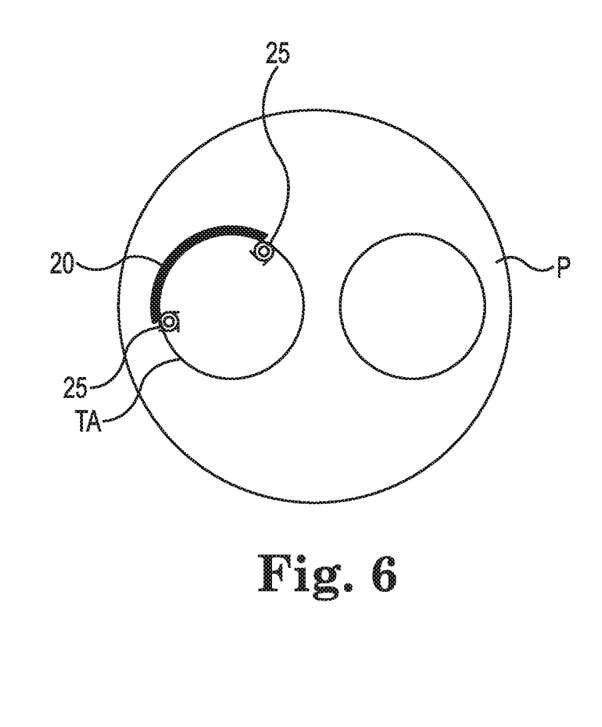
FIG. 6 is a schematic cross-sectional view of a penis with the implant illustrated in FIG. 5A positioned on the tunica albuginea of the penis.

FIG. 6 is a schematic cross-sectional view of a penis P including the tunica albuginea TA located around the corpora cavernosa CC of the penis P. The implant 20 is illustrated schematically and includes any of the devices described above suitably placed on the tunica albuginea TA on a side of one of the corpora cavernosa CC of the penis. The implant 20 has a semi-circular configuration 45 and/or provides a curved or crescent-shaped support for the penile tissue. Attachment mechanisms 25 attaching the implant 20 to the penis P are also shown.

Figure 7:
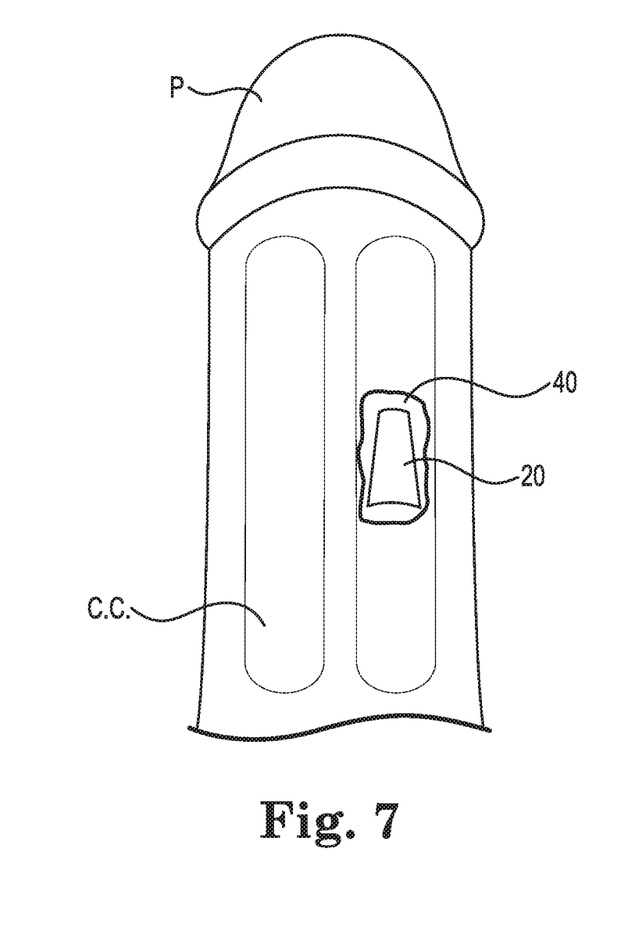
FIG. 7 is a schematic top view of a penis showing a position and a configuration of the implant illustrated in FIG. 5C implanted in the penis.

FIG. 7 is a top view illustrating the combined rhomboid/semi-circular configuration of the embodiment of FIG. 5C placed on an area of one of the corpora cavernosa CC of the penis P where the Peyronie's plaques has been removed from.

As further illustrated in FIG. 7, embodiments include an implant 20 that covers at least 25% of the area of the affected side 40 of the penis P. In case not all of the area from which the Peyronie's plaque has been removed needs to be covered or supported by the implant 20, the implant 20 suitably is configured to have a size of less than that area of excised tissue, however no less than 25% of that area. Due to the flexibility and strength of the implant 20, the penile tissue is supported sufficiently and effectively by a less bulky implant and thereby an implant of a size less than the affected area may suffice in some cases.

In an aspect, the application relates to a method of treating Peyronie's disease by providing an implant in the affected penis.

With additional reference to FIG. 1C, the erect penis P has a pair of corpora cavernosa CC that extend from a proximal location internal to the body up to a mid-location of the glans penis. The illustrated erect penis P includes plaques that have formed on an affected area on one side 40 of the penis P that cause the erect penis P to have an affected length La. The penis P has an unaffected side 42 that is generally opposite the affected side 40 of the penis. The unaffected side 42 of the penis P has an unaffected length of Lu. The affected side 40 of the erect penis is generally shorter than the unaffected side 42 of the erect penis such that the erect penis P presents with an undesirable curvature. FIG. 1C also illustrates an implant 20 to be used in the treatment of the penis P.

With additional reference to FIG. 1D, the penis P includes the implant 20 subcutaneously attached to penile tissue, e.g. the tunica albuginea TA, on the affected side 40 of the penis P. The implant 20 supports the penile tissue during the erection and provides for new tissue ingrowth in the implant.

In one embodiment, the implant 20 is attached subcutaneously to the tunica albuginea TA of a flaccid penis P. For example, the implant 20 is provided in a variety of sizes that allows the surgeon to select an implant 20 having the appropriate size based on pre-treatment measurements, and knowing these measurements, the surgeon selects the appropriately sized implant 20 for attachment to the flaccid penis P.

With additional reference to FIG. 1E, the erect penis P includes an implant 20 attached subcutaneously to the tunica albuginea on the affected side 40 of the Peyronie's afflicted penis to provide support for the penile tissue in an area from where the Peyronie's plaques has been excised, thereby straightening the penis P by obtaining an approximate equal length of both the affected and unaffected sides 40 and 42 of the penis P. Further, the flexible implant 20 allows for renewed tissue ingrowth so the penis P sustains repeated erections at a reduced risk of developing new Peyronie's plaques.

Figure 8:
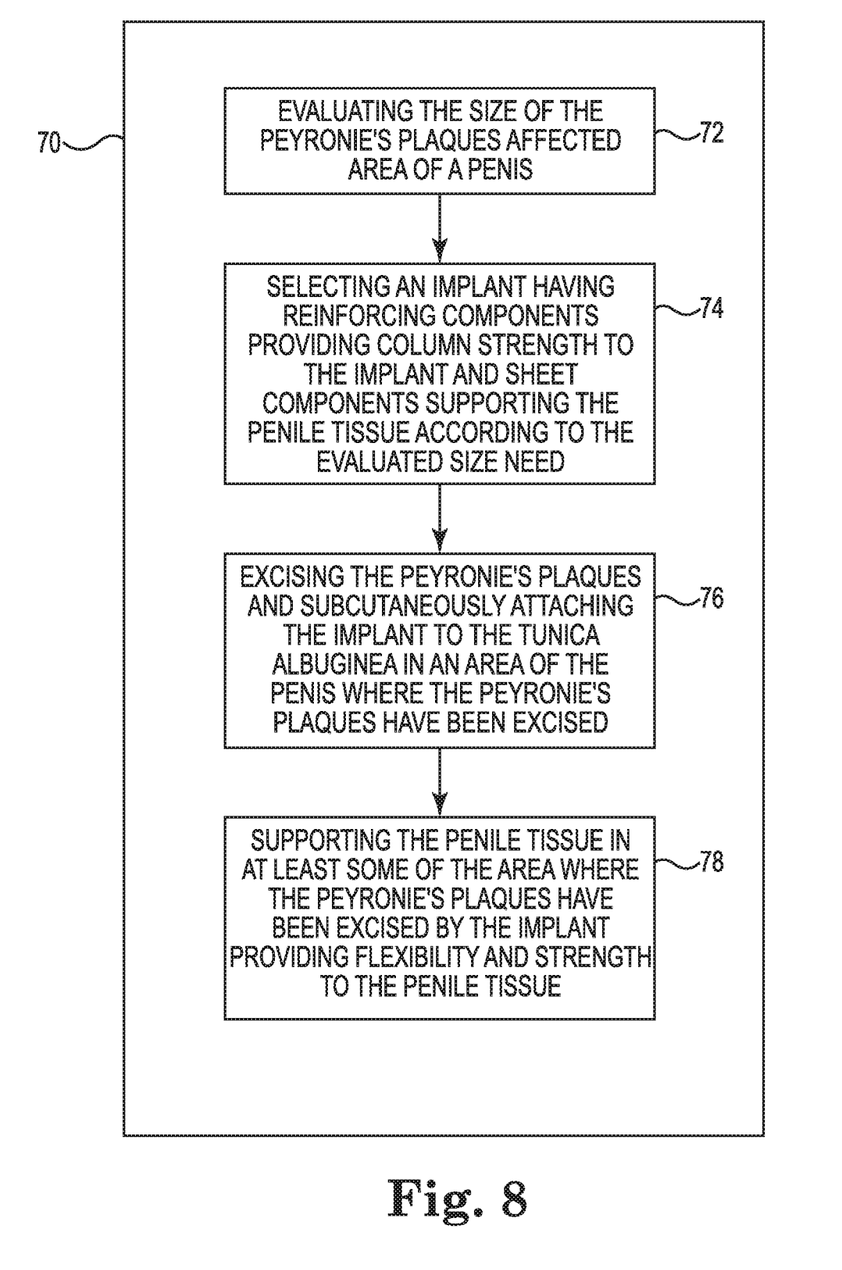
FIG. 8 is a block diagram of one embodiment of a method of treating Peyronie's disease.

FIG. 8 is a block diagram 70 of one embodiment of a method of treating Peyronie's disease. The method of treatment includes at 72 evaluating the size of the Peyronie's plaques affected area of a penis. The method of treatment includes at 74 selecting an implant 20 having reinforcing components 22 providing column strength to the implant 20 and sheet components supporting the penile tissue and promoting new tissue ingrowth. The method of treatment includes at 76 subcutaneously attaching the implant to the tunica albuginea in an area of the penis where the Peyronie's plaques has been excised thereby supporting the exposed penile tissue and avoiding the curvature of the penis P. The provides at 78 supporting the penile tissue where the Peyronie's plaques have been removed.

EXAMPLE

The following example illustrates, with reference to FIGS. 1C-1E, the surgical placement of one of the implants described above.

The patient is anesthetized and surgically draped to define a sterile operating field in an appropriate manner.

The surgeon forms a circumcoronal incision adjacent to the glans penis and a penoscrotal incision adjacent to the base of the penis P. The dartos fascia is reflected to expose the Buck's fascia, and the Buck's fascia is incised down to the tunica albuginea.

The surgeon excises the Peyronie's plaques, or scar tissue, from the affected area of the penis P.

After having evaluated and picked the required size and shape of the implant 20, the surgeon proceeds to attach one of the above-described Peyronie's treatment implants to an exterior surface of the tunica albuginea on an affected area of the penis on which the Peyronie's plaques have been excised.

In one embodiment, an artificial erection is imparted to the penis P with an intracavernous injection of saline solution before attaching the implant 20 to the penis P. In other embodiments, the implant 20 is attached to the penis P while the penis is its flaccid state.

As a result of the excision of the Peyronie's plaques, the curvature in the penis P on the plaque's affected side is reduced or eliminated. In order to maintain the penis P in this straightened condition, the implantation and attachment of the implant 20 to the penis P, provides support to the penile tissue in at least some of the area where the plaque's have been excised and provides flexibility and strengthens the column strength of the implant 20 in a direction parallel to, or along, the penis P. In this manner, the Peyronie's treatment implant provides support and strength to the penile tissue so that the corrected curvature of the penis P can be maintained.

The Peyronie's treatment implant provides an implant 20 that reduces or eliminates the formation of fibrosis tissue, or Peyronie's plaque. The implant is providing a biocompatible implant that has a high degree of flexibility and increased strength. The implant does not need subsequent surgical removal or substitution because it is accepted by the user's body and furthermore has improved strength, sustainability and durability.

This provides an implant that allows for tissue reconstruction and is less bulky and consequently less strenuous on the surrounding tissue of the penis once implanted. The implant eliminates or reduces the physical effects of the Peyronie's disease and improves patient perception and comfort.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An implant comprising:
    a reinforcement component attached to a sheet component, the sheet component formed as a porous and fibrous material, the implant adapted to be implanted on an area of a penis having Peyronie's plaques excised;
    wherein the reinforcement component includes a longitudinal rod and a transverse connector, with the longitudinal rod providing column strength to the implant and including a shape memory material configured to elongate during erection of the penis from a flaccid state to an erect state and contract during return from the erect state to the flaccid state, and
    wherein the sheet component is adapted to provide support for penile tissue.

2. The implant of claim 1, wherein the reinforcement component includes two longitudinal rods and two transverse connectors.

3. The implant of claim 2, wherein the reinforcement component provides a substantially rectangular framework with a first transverse connector attached to a distal end of each of the two longitudinal rods and a second transverse connector attached to a proximal end of each of the two longitudinal rods.

4. The implant of claim 2, wherein the two longitudinal rods and the two transverse connectors are fabricated as an integrated frame.

5. The implant of claim 1, limber comprising an attachment me chan s connected to one of the reinforcement component and the sheet component.

6. The implant of claim 5, wherein a first end of the attachment mechanism is fixedly connected to the reinforcement component and a second end of the attachment mechanism is configured for attachment to the penile tissue.

7. The implant of claim 5, wherein the attachment mechanism is a suture line coupled to a detachable needle.

8. The implant of claim 7, wherein the suture line includes an anchoring barb located on the suture line.

9. The implant of claim 1, wherein the sheet component includes a tissue-ingrowth promoter.

10. The implant of claim 1, further comprising two reinforcement components with the sheet component secured between the two reinforcement components.

11. The implant of claim 1, wherein the sheet component is disposed on the reinforcement component.

12. The implant of claim 1, wherein the longitudinal rod is circular in cross-section.

13. The implant of claim 1, wherein the sheet component has a cylinder shape.

14. The implant of claim 1, wherein an end of the longitudinal rod includes a radially extending flange.

15. The implant of claim 1, wherein the shape memory material has at least two stable states including a first state corresponding to the flaccid state of the penis and a second state corresponding to the erect state of the penis.

16. The implant of claim 15, wherein, when implanted on the area of the penis, the shape memory material is configured to transition from the first state to the second state when exposed to heat from blood flow into the corpora cavernosum that creates an erection of the penis causing the area of the penis to increase in temperature.

17. The implant of claim 15, wherein the shape memory material is configured to transition from the first state to the second state when exposed to electricity.

18. The implant of claim 1, wherein the shape memory material includes one or more materials selected from a group consisting of:
   Nitinol;
   a shape memory polymer; and
   a shape memory polymer based on polyurethane.

19. A method comprising:
   implanting a penile implant on an area of a penis having Peyronie's plaques excised,
   wherein the penile implant includes:
      a reinforcement component attached to a sheet component, the sheet component formed as a porous and fibrous material,
      wherein the reinforcement component includes a longitudinal rod and a transverse connector, with the longitudinal rod providing column strength to the implant and including a shape memory material configured to elongate during erection of the penis and contract when the penis returns to a flaccid state,
   wherein, following the implantation, the sheet component provides support for penile tissue.

20. The method of claim 19, wherein, once implanted on the area of the penis, the shape memory material is configured to transition from a first state corresponding to a flaccid state of the penis to a second state corresponding to an erect state of the penis when exposed to heat from blood flow into the corpora cavernosum that creates an erection of the penis causing the area of the penis to increase in temperature.

* * * * *

UNITED STATES PATENT AND TRADEMARK OFFICE
CERTIFICATE OF CORRECTION

PATENT NO. : 9,795,483 B2
APPLICATION NO. : 15/201512
DATED : October 24, 2017
INVENTOR(S) : Sarah J. Deitch and Julie M. Kerkvliet It is certified that error appears in the above-identified patent and that said Letters Patent is hereby corrected as shown below:

Claim 5 at Column 12, Line 46-47:
"The implant of claim 1, limber comprising" should read "The implant of claim 1, further comprising"; "an attachment me chan s connected" should read "an attachment mechanism connected"

Signed and Sealed this
Twenty-fourth Day of April, 2018

Andrei Iancu
*Director of the United States Patent and Trademark Office*